US007538235B2

(12) United States Patent
Lockemeyer

(10) Patent No.: US 7,538,235 B2
(45) Date of Patent: *May 26, 2009

(54) PROCESS FOR PREPARING A CATALYST, THE CATALYST, AND A USE OF THE CATALYST

(75) Inventor: John Robert Lockemeyer, Sugar Land, TX (US)

(73) Assignee: Shell Oil Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/096,117

(22) Filed: Mar. 31, 2005

(65) Prior Publication Data

US 2005/0222442 A1 Oct. 6, 2005

Related U.S. Application Data

(60) Provisional application No. 60/558,440, filed on Apr. 1, 2004.

(51) Int. Cl.
*C07D 301/10* (2006.01)
*C07D 301/03* (2006.01)
*C07D 27/00* (2006.01)
*C07D 31/00* (2006.01)

(52) U.S. Cl. ............ 549/534; 549/536; 502/166; 502/167; 502/169; 568/901; 568/907; 568/909.8

(58) Field of Classification Search ............ 549/534, 549/536; 502/169, 166, 167; 568/900, 901, 568/909.8
See application file for complete search history.

(56) References Cited

U.S. PATENT DOCUMENTS

| | | | |
|---|---|---|---|
| 2,238,474 A | 4/1941 | McNamee et al. | 260/348 |
| 2,424,083 A | 7/1947 | Finch et al. | 252/204 |
| 2,901,441 A | 8/1959 | Waterman | 252/463 |
| 3,563,913 A | 2/1971 | De Krijger et al. | 262/463 |
| 3,563,914 A | 2/1971 | Wattimena et al. | 252/463 |
| 3,844,981 A | 10/1974 | Cusumano | 252/471 |
| 3,895,093 A | 7/1975 | Weidenbach et al. | 423/213.5 |
| 3,962,136 A | 6/1976 | Nielsen et al. | 252/454 |
| 3,962,285 A | 6/1976 | Cusumano | 260/348.5 R |
| 3,972,829 A | 8/1976 | Michalko | 252/430 |
| 3,997,476 A | 12/1976 | Cull | 252/463 |
| 4,005,049 A | 1/1977 | Fields | 252/467 |
| 4,033,903 A | 7/1977 | Maxwell | 252/476 |
| 4,125,480 A | 11/1978 | Maxwell | 252/414 |
| 4,186,106 A | 1/1980 | Rebsdat et al. | 252/414 |
| 4,207,210 A | 6/1980 | Kilty | 252/463 |
| 4,212,772 A | 7/1980 | Mross et al. | 252/476 |
| 4,235,798 A | 11/1980 | Bartley et al. | 260/449 |
| 4,244,889 A | 1/1981 | Bartley et al. | 564/132 |
| 4,356,312 A | 10/1982 | Nieslen et al. | 549/534 |
| 4,361,500 A | 11/1982 | Mathe et al. | 252/430 |
| 4,361,503 A | 11/1982 | Dwyer et al. | 252/455 |
| 4,361,504 A | 11/1982 | Solomon et al. | 252/463 |
| 4,366,092 A | 12/1982 | Winterton | 252/476 |
| 4,366,093 A | 12/1982 | Shiozaki et al. | 252/477 |
| 4,367,167 A | 1/1983 | Lee et al. | 252/472 |
| 4,368,144 A | 1/1983 | Mitsuhata et al. | 252/463 |
| 4,379,134 A | 4/1983 | Weber et al. | 423/626 |
| 4,382,149 A | 5/1983 | Krueger | 568/473 |
| 4,420,420 A | 12/1983 | Mita et al. | 502/261 |
| 4,458,032 A | 7/1984 | Rebsdat et al. | 502/348 |
| 4,471,071 A | 9/1984 | Rebsdat et al. | 502/347 |
| 4,511,671 A | 4/1985 | Saito et al. | 502/242 |
| 4,532,231 A | 7/1985 | Johnson | 502/347 |
| 4,628,129 A | 12/1986 | Bartley | 568/864 |
| 4,645,754 A | 2/1987 | Tamura et al. | 502/527 |
| 4,656,157 A | 4/1987 | Hofmann et al. | 502/439 |
| 4,665,048 A | 5/1987 | Van Leeuwen et al. | 502/221 |
| 4,728,634 A | 3/1988 | Boxhoorn et al. | 502/243 |
| 4,731,350 A | 3/1988 | Boxhoorn et al. | 502/231 |
| 4,761,394 A | 8/1988 | Lauritzen | 502/348 |
| 4,766,105 A | 8/1988 | Lauritzen | 502/216 |
| 4,797,270 A | 1/1989 | Cendan et al. | 423/625 |
| 4,797,279 A | 1/1989 | Karamata et al. | 424/93 |
| 4,808,738 A | 2/1989 | Lauritzen | 549/536 |
| 4,810,689 A | 3/1989 | Hayden | 502/347 |
| 4,820,675 A | 4/1989 | Lauritzen | 502/216 |
| 4,829,044 A | 5/1989 | Boxhoorn et al. | 502/348 |

(Continued)

FOREIGN PATENT DOCUMENTS

DE  1920976  11/1969

(Continued)

OTHER PUBLICATIONS

B.E.T. (Brunner, Emmett and Teller) Journal of American Chemical Society 60 (1938) pp. 309-316.

(Continued)

*Primary Examiner*—Janet L. Andres
*Assistant Examiner*—Raymong Covington

(57) ABSTRACT

A process for preparing an epoxidation catalyst comprising silver and a high-selectivity dopant on a support, which process comprises depositing a base having a $pK_b$ of at most 3.5 when measured in water at 25° C., on the support prior to depositing silver on the support, and depositing silver and a high-selectivity dopant on the support;

the epoxidation catalyst; and a process for preparing an olefin oxide by reacting an olefin with oxygen in the presence of the epoxidation catalyst.

17 Claims, No Drawings

U.S. PATENT DOCUMENTS

| | | | |
|---|---|---|---|
| 4,837,194 A | 6/1989 | Hayden | 502/348 |
| 4,845,296 A | 7/1989 | Ahmed et al. | 564/477 |
| 4,874,739 A | 10/1989 | Boxhoorn | 502/218 |
| 4,886,917 A | 12/1989 | Knopf et al. | 568/623 |
| 4,908,343 A | 3/1990 | Bhasin | 502/218 |
| 4,916,243 A | 4/1990 | Bhasin et al. | 549/534 |
| 4,921,681 A | 5/1990 | Ozero et al. | 422/197 |
| 4,939,114 A | 7/1990 | Nojiri et al. | 502/348 |
| 4,939,144 A | 7/1990 | Coates et al. | 514/212 |
| 4,994,587 A | 2/1991 | Notermann et al. | 549/534 |
| 4,994,588 A | 2/1991 | Kapicak et al. | 549/534 |
| 4,994,589 A | 2/1991 | Notermann | 549/534 |
| 5,037,794 A | 8/1991 | Magistro | 502/355 |
| 5,055,442 A | 10/1991 | Osaka et al. | 502/439 |
| 5,057,481 A | 10/1991 | Bhasin | 502/208 |
| 5,100,859 A | 3/1992 | Gerdes et al. | 502/439 |
| 5,112,795 A | 5/1992 | Minahan et al. | 502/324 |
| 5,145,824 A | 9/1992 | Buffum et al. | 502/216 |
| 5,187,140 A | 2/1993 | Thorsteinson et al. | 502/348 |
| 5,254,786 A | 10/1993 | Lin et al. | 585/645 |
| 5,364,826 A | 11/1994 | Kemp | 502/315 |
| 5,374,748 A | 12/1994 | Rizkalla | 549/534 |
| 5,380,697 A | 1/1995 | Matusz et al. | 502/348 |
| 5,380,885 A | 1/1995 | Kemp | 549/536 |
| 5,387,751 A | 2/1995 | Hayden et al. | 549/534 |
| 5,407,888 A | 4/1995 | Herzog et al. | 502/317 |
| 5,418,202 A | 5/1995 | Evans et al. | 502/348 |
| 5,447,897 A | 9/1995 | Kemp | 502/303 |
| 5,457,897 A | 10/1995 | Becker | 34/472 |
| 5,486,628 A | 1/1996 | Kemp | 549/536 |
| 5,502,020 A | 3/1996 | Iwakura et al. | 502/317 |
| 5,545,603 A | 8/1996 | Kemp | 502/347 |
| 5,597,773 A | 1/1997 | Evans et al. | 502/348 |
| 5,663,385 A | 9/1997 | Kemp | 549/536 |
| 5,668,077 A | 9/1997 | Klopries et al. | 502/347 |
| 5,703,253 A | 12/1997 | Evans et al. | 549/536 |
| 5,705,661 A | 1/1998 | Iwakura et al. | 549/536 |
| 5,734,068 A | 3/1998 | Klopries et al. | 549/536 |
| 5,739,075 A | 4/1998 | Matusz | 502/302 |
| 5,801,259 A | 9/1998 | Kowaleski | 549/536 |
| 5,935,894 A | 8/1999 | Kanazirev | 502/341 |
| 6,103,916 A | 8/2000 | Takada et al. | 549/534 |
| 6,281,160 B1 | 8/2001 | Basset et al. | 502/332 |
| 6,325,919 B1 | 12/2001 | Koyama et al. | 208/134 |
| 6,368,998 B1 * | 4/2002 | Lockemeyer | 502/347 |
| 6,498,122 B2 | 12/2002 | Nakashiro | 502/347 |
| 6,511,938 B1 | 1/2003 | Liu et al. | 502/347 |
| 6,656,874 B2 | 12/2003 | Lockemeyer | 502/347 |
| 2002/0010094 A1 | 1/2002 | Lockemeyer | 502/439 |
| 2002/0010378 A1 | 1/2002 | Kakimoto et al. | 568/867 |
| 2002/0137957 A1 | 9/2002 | Lockemeyer | 549/534 |
| 2004/0224841 A1 | 11/2004 | Matusz et al. | 502/347 |
| 2004/0260103 A1 | 12/2004 | Matusz et al. | 549/534 |

FOREIGN PATENT DOCUMENTS

| | | |
|---|---|---|
| EP | 568978 | 1/1946 |
| EP | 211521 | 2/1987 |
| EP | 266015 | 5/1988 |
| EP | 563 414 A1 | 10/1993 |
| EP | 327356 | 3/1995 |
| EP | 716884 | 6/1996 |
| EP | 0716884 A2 | 6/1996 |
| EP | 0937498 A1 | 8/1999 |
| EP | 1002575 A2 | 5/2000 |
| EP | 1277698 A2 | 1/2003 |
| EP | 1201301 B1 | 3/2005 |
| FR | 2005978 | 10/1969 |
| GB | 1257352 | 12/1971 |
| GB | 1489335 | 10/1977 |
| JP | 56164013 | 12/1981 |
| WO | 96/23585 | 8/1996 |
| WO | 96/41848 | 12/1996 |
| WO | 02/26370 A1 | 4/2002 |
| WO | 03/072246 A2 | 9/2003 |
| WO | 2004/094055 A2 | 11/2004 |
| WO | 2004/101144 A1 | 11/2004 |
| WO | 2005/023417 A1 | 3/2005 |

OTHER PUBLICATIONS

"Kirk-Othmer Encyclopedia of Chemical Technology", 3rd edition, vol. 9, 1980, pp. 445-447.

International Search Report for PCT/US2005/010992 dated Jul. 18, 2005.

J.W. Fulton, "Selecting the Catalyst Configuration". Chemical Engineering. May 12, 1986. pp. 97-101.

* cited by examiner

PROCESS FOR PREPARING A CATALYST, THE CATALYST, AND A USE OF THE CATALYST

This application claims the benefit of U.S. Provisional Application No. 60/558,440 filed Apr. 1, 2004, the entire disclosure of which is hereby incorporated by reference.

FIELD OF THE INVENTION

The invention relates to a process for preparing an epoxidation catalyst, the catalyst per se and a process for the epoxidation of an olefin in which the catalyst is used.

BACKGROUND OF THE INVENTION

In olefin epoxidation an olefin is reacted with oxygen to form an olefin epoxide, using a silver-based catalyst. The olefin oxide may be reacted with water, an alcohol or an amine to form a 1,2-diol, a 1,2-diol ether or an alkanolamine. Thus, 1,2-diols, 1,2-diol ethers and alkanolamines may be produced in a multi-step process comprising olefin epoxidation and converting the formed olefin oxide with water, an alcohol or an amine.

Conventional silver-based catalysts have provided the olefin oxide notoriously in a low selectivity. For example, when using a conventional catalyst, the selectivity towards ethylene oxide, expressed as a fraction of the ethylene converted, does not reach values above the 6/7 or 85.7 mole-% limit. Therefore, this limit has long been considered to be the theoretically maximal selectivity of this reaction, based on the stoichiometry of the reaction equation

$7C_2H_4 + 6O_2 => 6C_2H_4O + 2CO_2 + 2H_2O$, cf. Kirk-Othmer's *Encyclopedia of Chemical Technology*, 3$^{rd}$ ed., Vol. 9, 1980, p. 445.

Further, the catalysts are subject to an aging-related performance decline during normal operation. The aging manifests itself by a reduction in the activity of the catalyst. Usually, when a reduction in activity of the catalyst is manifest, the reaction temperature is increased in order to compensate for the reduction in activity. The reaction temperature may be increased until it becomes undesirably high, at which point in time the catalyst is deemed to be at the end of its lifetime and would need to be exchanged.

Over the years much effort has been devoted to improving epoxidation catalysts in their performance, for example in respect of their initial activity and selectivity, and in respect of their stability performance, that is their resistance against the aging-related performance decline. Solutions have been found in improved compositions of the catalysts, and, in other instances, solutions have been found in improved processes of preparing the catalysts.

Modern silver-based catalysts are highly selective towards olefin oxide production. When using the modern catalysts in the epoxidation of ethylene the selectivity towards ethylene oxide can reach values above the 6/7 or 85.7 mole-% limit referred to hereinbefore. Such high-selectivity catalysts may comprise as their active components silver, and one or more high-selectivity dopants, such as components comprising rhenium, tungsten, chromium or molybdenum. High-selectivity catalysts are disclosed, for example, in U.S. Pat. No. 4,761,394 and U.S. Pat. No. 4,766,105.

In respect of improved processes, U.S. Pat. No. 6,368,998, for example, shows that washing the support with water, or first with aqueous base and then with water, prior to the deposition of silver, leads to epoxidation catalysts which have improved initial performance properties. A further improvement can be achieved by depositing silver by impregnating the support with a silver containing impregnation solution which has a higher pH than conventional, for example, having a measured pH of 13.2 or 13.6 by the presence therein of additional base in the form of hydroxide.

In particular the high-selectivity catalysts are subject to an aging-related performance decline during normal operation and they tend to be exchanged more frequently than the conventional catalysts. It goes without saying that from an economical point of view it is highly desirable to improve the initial performance and the lifetime of high-selectivity catalysts as much as possible.

SUMMARY OF THE INVENTION

The present invention provides a process for preparing an epoxidation catalyst comprising silver and a high-selectivity dopant on a support, which process comprises
 depositing a base having a $pK_b$ of at most 3.5 when measured in water at 25° C., on the support prior to depositing silver on the support, and
 depositing silver and a high-selectivity dopant on the support.

The invention also provides an epoxidation catalyst obtainable by the process of the invention.

The invention also provides a process for preparing an olefin oxide by reacting an olefin with oxygen in the presence of an epoxidation catalyst obtainable by the process of the invention.

The invention also provides a method of using an olefin oxide for making a 1,2-alkanediol, a 1,2-alkanediol ether or a 1,2-alkanolamine comprising converting the olefin oxide into the 1,2-alkanediol, the 1,2-alkanediol ether, or the 1,2-alkanolamine, wherein the olefin oxide has been obtained by a process for preparing an olefin oxide according to this invention.

DETAILED DESCRIPTION OF THE INVENTION

When a high-selectivity catalyst is prepared by depositing a base on the support prior to depositing silver, in accordance with the invention, an improvement is accomplished in the initial performance of the catalyst, in particular in the initial activity, compared with a conventional high-selectivity catalyst, i.e. prepared without depositing a base on the support prior to depositing silver. The catalyst may also show an advantage in aging relating performance during its use in a commercial olefin epoxidation process.

The support for use in this invention may be based on a wide range of materials. Such materials may be natural or artificial inorganic materials and they may include refractory materials, silicon carbide, clays, zeolites, charcoal and alkaline earth metal carbonates, for example calcium carbonate. Preferred are refractory materials, such as alumina, magnesia, zirconia and silica. The most preferred material is α-alumina. Typically, the support comprises at least 85% w, more typically 90% w, in particular 95% w α-alumina, frequently up to 99.9% w α-alumina, relative to the weight of the support. Other components of the α-alumina support may comprise, for example, silica, alkali metal components, for example sodium and/or potassium components, and/or alkaline earth metal components, for example calcium and/or magnesium components.

The surface area of the support may suitably be at least 0.1 m²/g, preferably at least 0.3 m²/g, more preferably at least 0.5 m²/g, and in particular at least 0.6 m²/g, relative to the weight of the support; and the surface area may suitably be at most 10 m²/g, preferably at most 5 m²/g, and in particular at most 3 m²/g, relative to the weight of the support. "Surface area" as used herein is understood to relate to the surface area as determined by the B.E.T. (Brunauer, Emmett and Teller) method as described in the Journal of the American Chemical Society 60 (1938) pp. 309-316. High surface area supports, in particular when they are α-alumina supports optionally comprising in addition silica, alkali metal and/or alkaline earth metal components, provide improved performance and stability of operation.

The water absorption of the support is typically in the range of from 0.2 to 0.8 g/g, preferably in the range of from 0.3 to 0.7 g/g. A higher water absorption may be favored in view of a more efficient deposition of silver and further elements, if any, on the support by impregnation. However, at a higher water absorption, the support, or the catalyst made therefrom, may have lower crush strength. As used herein, water absorption is deemed to have been measured in accordance with ASTM C20, and water absorption is expressed as the weight of the water that can be absorbed into the pores of the support, relative to the weight of the support.

The support is typically a calcined, i.e. sintered, support, preferably in the form of formed bodies, the size of which is in general determined by the dimensions of a reactor in which they are to be deposited. Generally however it is found very convenient to use particles such as formed bodies in the form of powdery particles, trapezoidal bodies, cylinders, saddles, spheres, doughnuts, and the like. The cylinders may be solid or hollow, straight or bent, and they may have their length and cross-sectional dimensions about the same and from 5 to 15 mm.

The performance of the catalyst may be enhanced if the support is washed before depositing catalyst ingredients on the support. On the other hand, unwashed supports may also be used successfully. A useful method for washing the support comprises washing the support in a continuous fashion with hot, demineralized water, until the electrical conductivity of the effluent water does not further decrease. A suitable temperature of the demineralized water is in the range of 80 to 100° C., for example 90° C. or 95° C. Alternatively, the support may be washed with base and subsequently with water. Reference may be made to U.S. Pat. No. 6,368,998, which is incorporated herein by reference.

The washing is intended to remove soluble residues from the support, in particular soluble residues which can be measured as nitric acid extractable components of the support. A method of measuring the content of nitric acid extractable components involves extracting a 10-gram sample of the support by boiling it with a 100 ml portion of 10% w nitric acid for 30 minutes (1 atm., i.e. 101.3 kPa) and determining in the combined extracts the relevant components by using a known method, for example atomic absorption spectroscopy. Reference is made to U.S. Pat. No. 5,801,259, which is incorporated herein by reference. The support for use in this invention, or more generally a support for preparing silver-based catalysts for use in the preparation of an olefin oxide from the olefin and oxygen, has typically a content of nitric acid extractable components (as the weight of the metal, or $SiO_2$), relative to the weight of the support; in parts per million (ppmw) as follows:

sodium: less than 500 ppmw, preferably less than 400 ppmw, and/or potassium: less than 150 ppmw, preferably less than 100 ppmw, and/or calcium: less than 400 ppmw, preferably less than 300 ppmw, and/or aluminum: less than 1100 ppmw, preferably less than 800 ppmw, and/or silicate: less than 1000 ppmw, preferably less than 800 ppmw.

If the support is a calcined support, in particular an α-alumina support, re-calcining the support may be an alternative method of reducing the content of nitric acid extractable components of the support. Suitably, the calcination is carried out by heating a precursor of the support at a temperature in the range of from 1000 to 1600° C., preferably 1200 to 1500° C., typically for a period of from 1 to 50 hours, and more typically from 10 to 40 hours. Suitably, the re-calcination may be carried out by heating the support at a similar temperature and for a similar period of time as in the calcination. Preferably, the conditions of re-calcination are somewhat less severe than the conditions of calcination, for example in that the temperature is 50° C. or 100° C. lower and/or the time is shorter. The atmosphere applied in the calcination or re-calcination is not critical. For example, an inert atmosphere may be applied, such as nitrogen or argon, or an oxygen containing atmosphere may be applied such as air or a mixture of air and nitrogen.

In accordance with this invention, a base (hereinafter "first base") is deposited on the support prior to depositing silver on the support. The first base has a $pK_b$ of at most 3.5, when measured in water at 25° C., preferably, the $pK_b$ is at most 2, more preferably at most 1. A suitable first base may be a hydroxide, for example lithium hydroxide or a quaternary ammonium hydroxide, typically tetramethylammonium hydroxide or tetraethylammonium hydroxide, or an alkoxide, typically lithium methoxide or aluminum trimethoxide. The quantity of first base may be up to 1000 mmole/kg support, for example in the range of from 0.5 to 500 mmole/kg support, preferably in the range of from 1 to 100 mmole/kg, more preferably in the range of from 5 to 50 mmole/kg, for example 10, 14, 20 or 30 mmole/kg.

The skilled person will appreciate that a base may be multibasic, that is having a multitude of basic functionalities. For example, a base may be dibasic or tribasic. The base properties of a multibasic compound may be specified using more than one $pK_b$ value. It is to be understood that, as used herein, in the case of a multibasic compound the number of moles of base having a $pK_b$ as specified includes the total number of moles of basic functionalities having the specified $pK_b$ value.

The first base may be deposited on the support by impregnating the support with a solution containing a sufficient amount of the first base. After impregnation, the support may be dried, typically at a temperature of at most 300° C., preferably at most 250° C., more preferably at most 200° C., and suitably at a temperature of at least 20° C., preferably at least 50° C., more preferably at least 80° C., suitably for a period of time of at least 1 minute, preferably at least 2 minutes, and suitably for a period of time of at most 60 minutes, preferably at most 30 minutes, more preferably at most 15 minutes. The application of more severe conditions, up to the calcination conditions, as described hereinbefore, may be considered in addition to, or in place of, the conditions described for the drying.

The volume of impregnation solutions described herein may be such that the support is impregnated until a point of incipient wetness of the support has been reached. Alternatively, a larger volume may be used and the surplus of solution may be removed from the wet support, for example by decantation or centrifugation. Amongst others, the impregnation solutions may comprise an alcoholic diluent, for example methanol of ethanol, or it may be aqueous. This includes that mixed diluents may be used.

The preparation of silver-based catalysts is known in the art and the known methods are applicable to the preparation of the catalyst in accordance with the invention. Methods of depositing silver on the support include impregnating the support with a silver compound containing cationic silver and performing a reduction to form metallic silver particles. Reference may be made, for example, to U.S. Pat. No. 5,380,697, U.S. Pat. No. 5,739,075, EP-A-266015 and U.S. Pat. No. 6,368,998, which US patents are incorporated herein by reference.

The reduction of cationic silver to metallic silver may be accomplished during a step in which the catalyst is dried, so that the reduction as such does not require a separate process step. This may be the case if the silver containing impregnation solution comprises a reducing agent, for example, an oxalate, as described in the Examples hereinafter. Such drying step is suitably carried out at a reaction temperature of at most 300° C., preferably at most 280° C., more preferably at most 260° C., and suitable at a reaction temperature of at least 200° C., preferably at least 210° C., more preferably at least 220° C., suitably for a period of time of at least 1 minute, preferably at least 2 minutes, and suitably for a period of time of at most 20 minutes, preferably at most 15 minutes, more preferably at most 10 minutes.

In preferred embodiment, amongst others, the silver containing impregnation solution comprises an added base (hereinafter "second base"), typically a base having a $pK_b$ of at most 3.5, when measured at 25° C., preferably at most 2, more preferably at most 1. A suitable second base may be a hydroxide, for example lithium hydroxide or a quaternary ammonium hydroxide, typically tetra-methylammonium hydroxide or tetraethylammonium hydroxide, or an alkoxide, typically lithium methoxide or aluminum trimethoxide. Preferably, the pH of the impregnation solution is at least 13.2, more preferably at least 14, in particular at least 14.5. As used herein, "pH" is the pH as measured at 20° C. The measured pH may be different from the true pH, because the medium of the solution in which the pH is measured may not be aqueous. The second base may be added to the impregnation solution in a quantity in the range of from 1 to 1000 mmole/kg support, preferably in the range of from 10 to 500 mmole/kg, more preferably in the range of from 50 to 100 mmole/kg, for example 70 or 75 mmole/kg.

The second base may or may not be the same as the first base.

Appreciable catalytic activity is obtained by employing a silver content of the catalyst of at least 10 g/kg, relative to the weight of the catalyst. Preferably, the catalyst comprises silver in a quantity of from 50 to 500 g/kg, more preferably from 100 to 400 g/kg, for example 105 g/kg, or 120 g/kg, or 190 g/kg, or 250 g/kg, or 350 g/kg, relative to the weight of the catalyst. The silver compound may be employed in the impregnation solution in a quantity sufficient to provide in a single deposition of silver a catalyst having a content of silver as disclosed herein. Alternatively, multiple depositions of silver may be applied, as further exemplified hereinafter.

The catalyst comprises, in addition to silver, one or more high-selectivity dopants. Catalysts comprising a high-selectivity dopant are known from U.S. Pat. No. 4,761,394 and U.S. Pat. No. 4,766,105, which are incorporated herein by reference. The high-selectivity dopants may comprise, for example, components comprising one or more of rhenium, molybdenum, chromium and tungsten. The high-selectivity dopants may be present in a total quantity of from 0.01 to 500 mmole/kg, calculated as the element (for example, rhenium, molybdenum, tungsten, and/or chromium) on the total catalyst. Rhenium, molybdenum, chromium or tungsten may suitably be provided as an oxide or as an oxyanion, for example, as a perrhenate, molybdate, tungstate, in salt or acid form. The high-selectivity dopants may be employed in the invention in a quantity sufficient to provide a catalyst having a content of high-selectivity dopant as disclosed herein.

Of special preference are catalysts which comprise a rhenium component, and optionally a rhenium co-promoter, in addition to silver. The rhenium component may typically be present in a quantity of at least 0.01 mmole/kg, more typically at least 0.1 mmole/kg, and preferably at least 0.5 mmole/kg, calculated as the quantity of rhenium relative to the weight of the catalyst. The rhenium component may be present in a quantity of at most 50 mmole/kg, preferably at most 10 mmole/kg, more preferably at most 5 mmole/kg, calculated as the quantity of rhenium relative to the weight of the catalyst. The rhenium co-promoter may suitably be selected from components which comprise one or more of tungsten, chromium, molybdenum, sulfur, phosphorus and boron. Preferably, the rhenium copomoter is selected from components which comprise one or more of tungsten, chromium, molybdenum and sulfur. It is particularly preferred that the rhenium co-promoter comprises a tungsten component. The rhenium co-promoter may typically be present in a total quantity of at least 0.01 mmole/kg, more typically at least 0.1 mmole/kg, and preferably at least 0.5 mmole/kg, calculated as the element (i.e. the total of tungsten, chromium, molybdenum, sulfur, phosphorus and/or boron), relative to the weight of the catalyst. The rhenium co-promoter may be present in a total quantity of at most 50 mmole/kg, preferably at most 10 mmole/kg, more preferably at most 5 mmole/kg, on the same basis. The form in which the rhenium co-promoter may be deposited is not material to the invention. For example, it may suitably be provided as an oxide or as an oxyanion, for example, as a sulfate, borate or molybdate, in salt or acid form. The rhenium component and the rhenium co-promoter may be employed in the invention in quantities sufficient to provide a catalyst having contents of the rhenium component and the rhenium co-promoter as disclosed herein.

The high-selectivity dopant may or may not be deposited on the support together with the deposition of silver. In the preparation of a catalyst having a relatively high silver content, for example in the range of from 150 to 500 g/kg, in particular from 200 to 400 g/kg, on total catalyst, it may be advantageous to apply multiple depositions of silver. Silver may be deposited in three or more portions, and preferably in two portions, which depositions may be together with or separate from the deposition of high-selectivity dopants. If a rhenium component and a rhenium co-promoter are present, a portion of silver may be deposited together with the deposition of the rhenium co-promoter, and another portion may be deposited together with the deposition of the rhenium component. Without wishing to be bound by theory, it is believed that in embodiments in which dopants (for example the rhenium component and/or the rhenium co-promoter) are deposited simultaneously with the deposition of a portion of silver, as opposed to deposition separate from the deposition of silver, a more favorable distribution of the dopant over the support will be achieved. Such embodiments are therefore preferred, as they will yield better catalysts. Silver may be divided over the various depositions, such that in each deposition a silver solution of the same silver concentration is employed. It is preferred, however, to employ in a later deposition a silver solution having a higher silver concentration than in a previous deposition.

The catalyst preferably comprises, in addition to silver and a high-selectivity dopant, a component comprising a further element. Eligible further elements may be selected from the group of nitrogen, fluorine, alkali metals, alkaline earth metals, titanium, hafnium, zirconium, vanadium, thallium, thorium, tantalum, niobium, gallium and germanium and mixtures thereof. Preferably the alkali metals are selected from lithium, potassium, rubidium and cesium. Most preferably the alkali metal is lithium, potassium and/or cesium. Preferably the alkaline earth metals are selected from calcium and barium. Typically, the further element is present in the catalyst in a total quantity of from 0.01 to 500 mmole/kg, more typically from 0.05 to 100 mmole/kg, calculated as the element on the catalyst. Where possible, the component comprising the further element may suitably be provided as an oxide or as an oxyanion, for example, as a sulfate, nitrate, nitrite, borate or molybdate, in salt or acid form. Salts of alkali metals or alkaline earth metals are suitable. The component comprising the further element may be employed in the invention in a quantity sufficient to provide a catalyst having a content of the further element as disclosed herein. The further element may be deposited on the support prior to, together with or after the deposition of silver; and/or prior to, together with or after the deposition of the high-selectivity dopant.

The content of alkali metal components of the catalyst generally influences the performance of the catalyst in the preparation of an olefin oxide from the olefin and oxygen. In one aspect, the performance may relate to the ability to operate the catalyst outside the conditions of a runaway reaction, that is total oxygen conversion and locally a very high catalyst temperature. In certain embodiments relating to catalysts which do not comprise a rhenium component or have a content of a rhenium component of less than 1.5 mmole/kg, in particular less than 1 mmole/kg, calculated as the quantity of rhenium relative to the weight of the catalyst, a cesium component may be applied in a quantity higher than the quantity that may be needed for optimal catalyst performance in terms of activity and selectivity (for example, 700 ppmw, instead of 500 ppmw, as the weight of cesium relative to the weight of the catalyst) with the effect that conditions of a runaway reaction are more easily avoided.

As used herein, the quantity of alkali metal present in the catalyst is deemed to be the quantity in so far as it can be extracted from the catalyst with de-ionized water at 100° C. The extraction method involves extracting a 10-gram sample of the catalyst three times by heating it in 20 ml portions of de-ionized water for 5 minutes at 100° C. and determining in the combined extracts the relevant metals by using a known method, for example atomic absorption spectroscopy.

As used herein, the quantity of alkaline earth metal present in the catalyst is deemed to be the quantity in so far as it can be extracted from the catalyst with 10% w nitric acid in de-ionized water at 100° C. The extraction method involves extracting a 10-gram sample of the catalyst by boiling it with a 100 ml portion of 10% w nitric acid for 30 minutes (1 atm., i.e. 101.3 kPa) and determining in the combined extracts the relevant metals by using a known method, for example atomic absorption spectroscopy. Reference is made to U.S. Pat. No. 5,801,259, which is incorporated herein by reference.

Although the present epoxidation process may be carried out in many ways, it is preferred to carry it out as a gas phase process, i.e. a process in which the feed is contacted in the gas phase with the catalyst which is present as a solid material, typically in a packed bed. Generally the process is carried out as a continuous process.

The olefin for use in the present epoxidation process may be any olefin, such as an aromatic olefin, for example styrene, or a di-olefin, whether conjugated or not, for example 1,9-decadiene or 1,3-butadiene. Typically, the olefin is a monoolefin, for example 2-butene or isobutene. Preferably, the olefin is a mono-α-olefin, for example 1-butene or propylene. The most preferred olefin is ethylene.

The olefin concentration in the feed may be selected within a wide range. Typically, the olefin concentration in the feed will be at most 80 mole-%, relative to the total feed. Preferably, it will be in the range of from 0.5 to 70 mole-%, in particular from 1 to 60 mole-%, on the same basis. As used herein, the feed is considered to be the composition which is contacted with the catalyst.

The present epoxidation process may be air-based or oxygen-based, see "Kirk-Othmer Encyclopedia of Chemical Technology", $3^{rd}$ edition, Volume 9, 1980, pp. 445-447. In the air-based process air or air enriched with oxygen is employed as the source of the oxidizing agent while in the oxygen-based processes high-purity (at least 95 mole-%) oxygen is employed as the source of the oxidizing agent. Presently most epoxidation plants are oxygen-based and this is a preferred embodiment of the present invention.

The oxygen concentration in the feed may be selected within a wide range. However, in practice, oxygen is generally applied at a concentration which avoids the flammable regime. Typically, the concentration of oxygen applied will be within the range of from 1 to 15 mole-%, more typically from 2 to 12 mole-% of the total feed.

In order to remain outside the flammable regime, the concentration of oxygen in the feed may be lowered as the concentration of the olefin is increased. The actual safe operating ranges depend, along with the feed composition, also on the reaction conditions such as the reaction temperature and the pressure.

An organic halide may be present in the feed as a reaction modifier for increasing the selectivity, suppressing the undesirable oxidation of olefin or olefin oxide to carbon dioxide and water, relative to the desired formation of olefin oxide. Organic halides are in particular organic bromides, and more in particular organic chlorides. Preferred organic halides are chlorohydrocarbons or bromohydrocarbons. More preferably they are selected from the group of methyl chloride, ethyl chloride, ethylene dichloride, ethylene dibromide, vinyl chloride or a mixture thereof. Most preferred are ethyl chloride and ethylene dichloride.

The organic halides are generally effective as reaction modifier when used in low concentration in the feed, for example up to 0.01 mole-%, relative to the total feed. In particular when the olefin is ethylene, it is preferred that the organic halide is present in the feed at a concentration of at most $50 \times 10^{-4}$ mole-%, in particular at most $20 \times 10^{-4}$ mole-%, more in particular at most $15 \times 10^{-4}$ mole-%, relative to the total feed, and preferably at least $0.2 \times 10^{-4}$ mole-%, in particular at least $0.5 \times 10^{-4}$ mole-%, more in particular at least $1 \times 10^{-4}$ mole-%, relative to the total feed.

In addition to the olefin, oxygen and the organic halide, the feed may contain one or more optional components, for example carbon dioxide, inert gases and saturated hydrocarbons. Carbon dioxide is a by-product in the epoxidation process. However, carbon dioxide generally has an adverse effect on the catalyst activity. Typically, a concentration of carbon dioxide in the feed in excess of 25 mole-%, preferably in excess of 10 mole-%, relative to the total feed, is avoided. A concentration of carbon dioxide as low as 1 mole-% or lower, for example 0.5 mole-%, relative to the total feed, may be employed. Inert gases, for example nitrogen or argon, may be present in the feed in a concentration of from 30 to 90 mole-%, typically from 40 to 80 mole-%. Suitable saturated hydrocarbons are methane and ethane. If saturated hydrocarbons are present, they may be present in a quantity of up to 80 mole-%, relative to the total feed, in particular up to 75 mole-%. Frequently they are present in a quantity of at least 30 mole-%, more frequently at least 40 mole-%. Saturated hydrocarbons may be added to the feed in order to increase the oxygen flammability limit.

The epoxidation process may be carried out using reaction temperatures selected from a wide range. Preferably the reaction temperature is in the range of from 150 to 340° C., more preferably in the range of from 180 to 325° C.

In order to reduce the effects of deactivation of the catalyst, the reaction temperature may be increased gradually or in a plurality of steps, for example in steps of from 0.1 to 20° C., in particular 0.2 to 10° C., more in particular 0.5 to 5° C. The total increase in the reaction temperature may be in the range of from 10 to 140° C., more typically from 20 to 100° C. The reaction temperature may be increased typically from a level in the range of from 150 to 300° C., more typically from 200 to 280° C., when a fresh catalyst is used, to a level in the range of from 230 to 340° C., more typically from 240 to 325° C., when the catalyst has decreased in activity due to aging.

The epoxidation process is preferably carried out at a reactor inlet pressure in the range of from 1000 to 3500 kPa. "GHSV" or Gas Hourly Space Velocity is the unit volume of gas at normal temperature and pressure (0° C., 1 atm, i.e. 101.3 kPa) passing over one unit volume of packed catalyst per hour. Preferably, when the epoxidation process is as a gas phase process involving a packed catalyst bed, the GHSV is in the range of from 1500 to 10000 Nl/(l.h). Preferably, the process is carried out at a work rate in the range of from 0.5 to 10 kmole olefin oxide produced per $m^3$ of catalyst per hour, in particular 0.7 to 8 kmole olefin oxide produced per $m^3$ of catalyst per hour, for example 5 kmole olefin oxide produced per $m^3$ of catalyst per hour.

The olefin oxide produced may be recovered from the reaction mixture by using methods known in the art, for example by absorbing the olefin oxide from a reactor outlet stream in water and optionally recovering the olefin oxide from the aqueous solution by distillation. At least a portion of the aqueous solution containing the olefin oxide may be applied in a subsequent process for converting the olefin oxide into a 1,2-diol, a 1,2-diol ether or an alkanolamine.

The olefin oxide produced in the epoxidation process may be converted into a 1,2-diol, into a 1,2-diol ether or into an alkanolamine.

The conversion into the 1,2-diol or the 1,2-diol ether may comprise, for example, reacting the olefin oxide with water, suitably using an acidic or a basic catalyst. For example, for making predominantly the 1,2-diol and less 1,2-diol ether, the olefin oxide may be reacted with a ten fold molar excess of water, in a liquid phase reaction in presence of an acid catalyst, e.g. 0.5-1.0% w sulfuric acid, based on the total reaction mixture, at 50-70° C. at 100 kPa absolute, or in a gas phase reaction at 130-240° C. and 2000-4000 kPa absolute, preferably in the absence of a catalyst. If the proportion of water is lowered the proportion of 1,2-diol ethers in the reaction mixture is increased. The 1,2-diol ethers thus produced may be a di-ether, tri-ether, tetra-ether or a subsequent ether. Alternative 1,2-diol ethers may be prepared by converting the olefin oxide with an alcohol, in particular a primary alcohol, such as methanol or ethanol, by replacing at least a portion of the water by the alcohol.

The conversion into the alkanolamine may comprise reacting the olefin oxide with an amine, such as ammonia, an alkyl amine or a dialkylamine. Anhydrous or aqueous ammonia may be used. Anhydrous ammonia is typically used to favor the production of monoalkanolamine. For methods applicable in the conversion of the olefin oxide into the alkanolamine, reference may be made to, for example U.S. Pat. No. 4,845,296, which is incorporated herein by reference.

The 1,2-diol and the 1,2-diol ether may be used in a large variety of industrial applications, for example in the fields of food, beverages, tobacco, cosmetics, thermoplastic polymers, curable resin systems, detergents, heat transfer systems, etc. The alkanolamine may be used, for example, in the treating ("sweetening") of natural gas.

Unless specified otherwise, the organic compounds mentioned herein, for example the olefins, 1,2-diols, 1,2-diol ethers, alkanolamines and organic halides, have typically at most 40 carbon atoms, more typically at most 20 carbon atoms, in particular at most 10 carbon atoms, more in particular at most 6 carbon atoms. As defined herein, ranges for numbers of carbon atoms (i.e. carbon number) include the numbers specified for the limits of the ranges.

Having generally described the invention, a further understanding may be obtained by reference to the following examples, which are provided for purposes of illustration only and are not intended to be limiting unless otherwise specified.

EXAMPLES 1-2 (EXAMPLE 1 FOR COMPARISON, EXAMPLE 2 ACCORDING TO THE INVENTION)

Preparation of Catalysts

Impregnation solutions were prepared by adding aqueous solutions comprising predetermined quantities of lithium nitrate, ammonium perrhenate, ammonium metatungstate, cesium hydroxide, and water to samples of a silver-amine-oxalate stock solution. The quantities were predetermined by calculation based on the desired composition of the catalyst to be prepared. The silver-amine-oxalate stock solution was prepared as described in U.S. Pat. No. 4,766,105, which is incorporated herein by reference.

Samples of an α-alumina support having a surface area of 0.77 $m^2$/g and a water absorption of 0.47 g/g, prepared according to U.S. Pat. No. 5,145,824, which is incorporated herein by reference, were impregnated with the impregnation solution and dried, as follows. The support samples (each approximately 30 g) were placed under a 25 mm Hg vacuum for 1 minute at ambient temperature. Approximately 50 g of an impregnating solution, prepared as indicated hereinbefore, was then introduced to submerse the support, and the vacuum was maintained at 25 mm Hg for an additional 3 minutes. The vacuum was then released and the excess impregnating solution was removed from the catalyst pre-cursor by centrifugation at 500 rpm for two minutes. The catalyst pre-cursor was then dried while being shaken at 250° C. for 5.5 minutes in a stream of air. The catalyst so prepared contained 13.2% w silver, 1.5 mmole/kg rhenium, 0.75 mmole/kg tungsten, 15 mmole/kg lithium, and 3.5 mmole/kg cesium, relative to the weight of the catalyst (Example 1).

This procedure was repeated with the difference that prior to contacting the support with the silver containing impregnation solution, the support was subjected to a procedure of impregnation and drying, as described in the previous paragraph, using an impregnation solution which contained tetraethylammonium hydroxide only, in a quantity of 14 mmole/kg, relative to the weight of the support (Example 2).

Catalyst Testing

The catalysts so prepared were tested in the production of ethylene oxide from ethylene and oxygen. To do this, 3.5 to 4.5 g of crushed catalyst were loaded into a stainless steel U-shaped tube. The tube was immersed in a molten metal bath (heat medium) and the ends were connected to a gas flow system. A gas or gas mixture passed through the catalyst bed, in a "once-through" operation. The weight of catalyst used and the inlet gas flow rate were adjusted to give a gas hourly space velocity of 3300 Nl/(l.h), as calculated for uncrushed catalyst. The inlet gas pressure was 1550 kPa absolute.

First, the catalysts were pretreated at 225° C. for 3 hours with nitrogen, and then the composition of the gas mixture was adjusted to 30% v ethylene, 8% v oxygen, 5% v carbon dioxide, 2.5 ppmv ethyl chloride, and nitrogen balance.

The reactor temperature was ramped up at a rate of 10° C. per hour to 245° C. and then the temperature was adjusted so as to achieve an ethylene oxide content of 3.1% v in the outlet gas stream. The ethyl chloride concentration in the gas mixture was adjusted between 2.5 and 5 ppmv so as to obtain an optimum selectivity at a constant ethylene oxide concentration in the outlet gas stream. The temperature was slowly increased to compensate for a decline in catalyst performance as a result of aging, i.e. such that a constant ethylene oxide content in the outlet gas stream was maintained.

For the catalysts the performance values for selectivity and temperature are reported in Table I, hereinafter. The performance values have been specified as an initial performance, i.e. after about a week of testing. A lower temperature needed to accomplish a certain ethylene oxide (EO) content in the outlet gas stream is indicative for a higher activity of the catalyst.

TABLE I

|  | Example 1 [1] | Example 2 [2] |
|---|---|---|
| Ingredients in impregnation solution: | | |
| First impregnation | Silver, rhenium, tungsten, lithium, cesium | Tetraethylammonium hydroxide |
| Second impregnation | (not applicable) | Silver, rhenium, tungsten, lithium, cesium |
| Catalyst performance: | | |
| Temperature (° C.) | 258 | 253 |
| Selectivity (%-mole) | 87.9 | 88.0 |

[1]) For comparison
[2]) According to invention

The Examples show that when, in accordance with the invention, a catalyst is prepared by depositing a base on the support prior to depositing silver (cf. Example 2), an improved catalyst performance is obtained in respect of the initial performance of the catalyst, in particular activity, compared with a catalyst which is prepared without depositing the base prior to depositing silver (cf. Example 1).

I claim:

1. A process for preparing an epoxidation catalyst comprising silver and a high-selectivity dopant on a support, which process comprises
depositing a base having a $pK_b$ of at most 3.5 when measured in water at 25° C., on the support prior to depositing silver on the support, which base is a quaternary ammonium hydroxide or an alkoxide and is deposited in a quantity of at least 5 mmole/kg of the support, and subsequently depositing silver and a high-selectivity dopant on the support.

2. The process as claimed in claim 1, wherein the base is deposited in a quantity of from at least 5 mmole/kg and up to 1000 mmole/kg of the support.

3. The process as claimed in claim 1, wherein the base is deposited in a quantity in the range of from 5 to 100 mmole/kg of the support.

4. The process as claimed in claim 1, wherein the base has a $pK_b$ of at most 2, when measured in water at 25° C.

5. The process as claimed in claim 4, wherein the base has a $pK_b$ of at most 1, when measured in water at 25° C.

6. The process as claimed in claim 1, wherein the base is an alkoxide.

7. The process as claimed in claim 6, wherein the base is a quaternary ammonium hydroxide.

8. The process as claimed in claim 1, wherein silver is deposited in a quantity in the range of from 100 to 400 g/kg, relative to the weight of the catalyst.

9. The process as claimed in claim 1, wherein the high-selectivity dopant comprises one or more of rhenium, molybdenum, chromium and tungsten.

10. The process as claimed in claim 9, wherein the high-selectivity dopant is deposited in a quantity sufficient to provide a catalyst having a total content of high-selectivity dopant of from 0.01 to 500 mmole/kg, calculated as the element, that is the total of rhenium, molybdenum, chromium and/or tungsten, on the total catalyst.

11. The process as claimed in claim 9, wherein the high-selectivity dopant comprises rhenium, and wherein in addition a rhenium co-promoter comprising one or more of tungsten, chromium, molybdenum, sulfur, phosphorous and boron is deposited on the support.

12. The process as claimed in claim 11, wherein the rhenium component and the rhenium co-promoter are deposited in a quantity sufficient to provide a catalyst having a content of the rhenium component in the range of from 0.01 to 50 mmole/kg, calculated as the quantity of rhenium relative to the weight of the catalyst, and having a total content of the rhenium co-promoter in the range of from 0.01 to 50 mmole/kg, calculated as the element, that is the total of tungsten, chromium, molybdenum, sulfur, phosphorus and/or boron, relative to the weight of the catalyst.

13. The process as claimed in claim 12, wherein the rhenium component and the rhenium co-promoter are deposited in a quantity sufficient to provide a catalyst having a content of the rhenium component in the range of from 0.1 to 10 mmole/kg, calculated as the quantity of rhenium relative to the weight of the catalyst, and having a total content of the rhenium co-promoter in the range of from 0.1 to 10 mmole/kg, calculated as the element, that is the total of tungsten, chromium, molybdenum, sulfur, phosphorus and/or boron, relative to the weight of the catalyst.

14. A process for preparing an olefin oxide by reacting an olefin with oxygen in the presence of an epoxidation catalyst, wherein the catalyst is prepared by a process which comprises
depositing a base having a $pK_b$ of at most 3.5 when measured in water at 25° C., on the support prior to depositing silver on the support, which base is a quaternary ammonium hydroxide or an alkoxide and is deposited in a quantity of at least 5 mmole/kg of the support, and
subsequently depositing silver and a high-selectivity dopant on the support.

15. A process for producing a 1,2-alkanediol, a 1,2-alkanediol ether or a 1,2-alkanolamine comprising:

obtaining an olefin oxide by reacting an olefin with oxygen in the presence of a catalyst, wherein the catalyst is prepared by a process which comprises depositing a base having a $pK_b$ of at most 3.5 when measured in water at 25°C., on the support prior to depositing silver on the support, which base is a quaternary ammonium hydroxide or an alkoxide and is deposited in a quantity of at least 5 mmole/kg of the support, and subsequently depositing silver and a high-selectivity dopant on the support; and converting the olefin oxide into the 1,2-alkanediol, the 1,2-alkanediol ether, or the 1,2-alkanolamine.

16. The process as claimed in claim 1, wherein the base is deposited in a quantity in the range of from 10 to 50 mmole/kg of the support.

17. The process as claimed in claim 1, wherein the base is deposited in a quantity in the range of from 10 to 30 mmole/kg of the support.

* * * * *